(12) United States Patent
Koraichi et al.

(10) Patent No.: US 8,604,930 B2
(45) Date of Patent: Dec. 10, 2013

(54) SENSOR DEVICE

(75) Inventors: Najib Koraichi, Schimmert (NL); Javier Montaner, Zaragoza (ES)

(73) Assignee: Vodafone Holding GmbH, Dussedorf (DE)

( * ) Notice: Subject to any disclaimer, the term of this patent is extended or adjusted under 35 U.S.C. 154(b) by 363 days.

(21) Appl. No.: 12/842,751

(22) Filed: Jul. 23, 2010

(65) Prior Publication Data
US 2011/0221595 A1 Sep. 15, 2011

(30) Foreign Application Priority Data
Mar. 10, 2010 (EP) .................................... 10002487

(51) Int. Cl.
*G08B 23/00* (2006.01)

(52) U.S. Cl.
USPC ................. 340/573.1; 340/573.4; 340/572.1; 340/5.1; 340/8.1; 340/539.12; 235/380; 235/382; 235/385; 235/492; 600/300; 600/301

(58) Field of Classification Search
USPC .............. 340/573.1, 573.4, 572.1–572.8, 5.1, 340/8.1, 539.12; 235/380, 382, 385, 492; 705/67; 600/300, 301
See application file for complete search history.

(56) References Cited

U.S. PATENT DOCUMENTS

| | | | | |
|---|---|---|---|---|
| 7,382,247 B2 * | 6/2008 | Welch et al. | ............. | 340/539.12 |
| 7,912,537 B2 * | 3/2011 | Lee et al. | ........................ | 600/547 |
| 8,161,290 B2 * | 4/2012 | McQuaide, Jr. | ............... | 713/186 |
| 2007/0131759 A1 * | 6/2007 | Cox et al. | ....................... | 235/380 |
| 2010/0291909 A1 * | 11/2010 | Nagaraja | ....................... | 455/415 |

* cited by examiner

*Primary Examiner* — Tai T Nguyen
(74) *Attorney, Agent, or Firm* — International IP Law Group, PLLC

(57) ABSTRACT

There is provided a mobile communication device. An exemplary mobile communication device comprises an input unit, a display and a processing unit being connected with a subscriber identity module and with an adapter module, wherein the adapter module is in communication with at least one sensor capturing biological and/or medical data of the user of the mobile communication device.

13 Claims, 4 Drawing Sheets

SENSOR DEVICE

CROSS REFERENCE TO RELATED APPLICATION

This application claims priority to European (EP) Patent Application No. 10 002 487.6, filed on Mar. 10, 2010, the contents of which are incorporated by reference as if set forth in their entirety herein.

BACKGROUND

Known telephones include so-called sensor telephones, which collect biological and/or medical data from sensors on a human body or from sensors which are located on the surface of the telephone. The data captured by the sensors are either just recorded for a later read out and processing of these data. The advantage is that a data such as blood pressure, skin resistance etc. can easily be captured over a longer period of time without requiring a dedicated medical device for doing that. In other types of such sensor phones the data undergo simple processing steps such as comparing the captured data with predetermined threshold values and notifying the user that a certain parameter exceeds its threshold value. In even more sophisticated sensor phones the data are sent to a network server, which provides feedback according to the interpretation of these data. Applications interpreting these data which are running on the server may use much more computing resources then those applications which are used on the mobile phone for interpretation purposes.

From the German patent application DE 10042101 A1, capturing and interpreting biological information about the user of a mobile communication device is known. The method relies on a communication device which is provided with biological sensors which are mounted on the surface of the mobile communication device in areas which are touched by the user of the communication device in normal operation. These sensors capture biological parameters such as blood pressure, heart frequency, body temperature and some blood values. The captured data which is stored on a chip allow evaluation of those values over a longer period of time. In addition to that the infringement of threshold values is immediately indicated to the user of the communication device. Finally, the communication device is adapted to notify the emergency room of a hospital in emergency cases. The notification comprises predefined standard texts.

In the international patent application WO 03/094720 A1 a cell phone device for remote monitoring of cardiac electrical activity is described. The device comprises a regular mobile telephone device which is introduced into a harness which is provided with necessary sensors to capture biological and/or medical parameters of the user of the device. In addition to that the harness is equipped with a controller, a memory and a modulator. The controller controls the timing of data submission into the telephone device and uses the memory to prevent loss of biological data. The modulator prepares the captured data signal for a submission to the telephone device input. The conditioned signal is in acoustic form.

Devices as those described above and which are known in the prior art either require a deep integration into the mobile phone impacting both hardware and software of the mobile phone or suffer from limitations with regard to the data communication capabilities.

Consequently, there remains a desire to conceive a mobile communication device allowing capturing biological and/or medical data of the user of the mobile communication device with a limited impact on the hardware and software of a conventional mobile communication device.

SUMMARY

Exemplary embodiments of the invention relate to a mobile communication device which is ranged to collect biological and/or medical data of the user of the mobile communication device. A system according to an exemplary embodiment may comprise a mobile communication device and a sensor capturing biological and/or medical data of the user of the mobile communication device.

In one exemplary embodiment of the invention, a mobile communication device comprises a sensor. The exemplary mobile communication device comprises an input unit, a display and a processing unit being connected with a subscriber identity module and with an adapter module, wherein the adapter module is in communication with the sensor capturing biological and/or medical data of the user of the mobile communication device.

The mobile communication device may desirably comprise a plurality of sensors. The sensor(s) may be located on the outside of the mobile communication device to provide physical contact with the user who utilizes the communication device.

In another exemplary embodiment of the invention, at least one sensor is not located on the mobile communication device. In this case, the sensor may be integrated in a device which is separate of the mobile communication device.

In an exemplary embodiment, the sensor, which may be separate of the mobile communication device, is connected to the adapter module by a data communication link. The communication link may be a wired or a wireless data communication link.

In one exemplary embodiment, the wireless data communication link may comprise a communication link according to the ZigBee or NFC standard.

In another exemplary embodiment of the invention, the adapter module is arranged to run an application for reading out the one sensor or the plurality of sensors connected to the mobile communication device.

A system according to an exemplary embodiment may comprise a communication device and a sensor. The communication device may include a subscriber identity module and an adapter module which is connected to the subscriber identity module. The adapter module is arranged to read out a sensor capturing biological and/or medical data of the user of the mobile communication device.

The adapter module and sensor may be each connected to a radio interface. In this case the radio interface may be an interface according to the ZigBee and/or NFC standard.

BRIEF DESCRIPTION OF THE DRAWINGS

The aforementioned and other aspects of the invention will also be apparent from and elucidated with reference to the embodiments described hereinafter making reference to the drawings. Reference will be made by way of example to the accompanying drawings in which.

In the drawings, similar elements and features are labelled with the same reference numbers.

DETAILED DESCRIPTION OF SPECIFIC EMBODIMENTS

Figure 1:
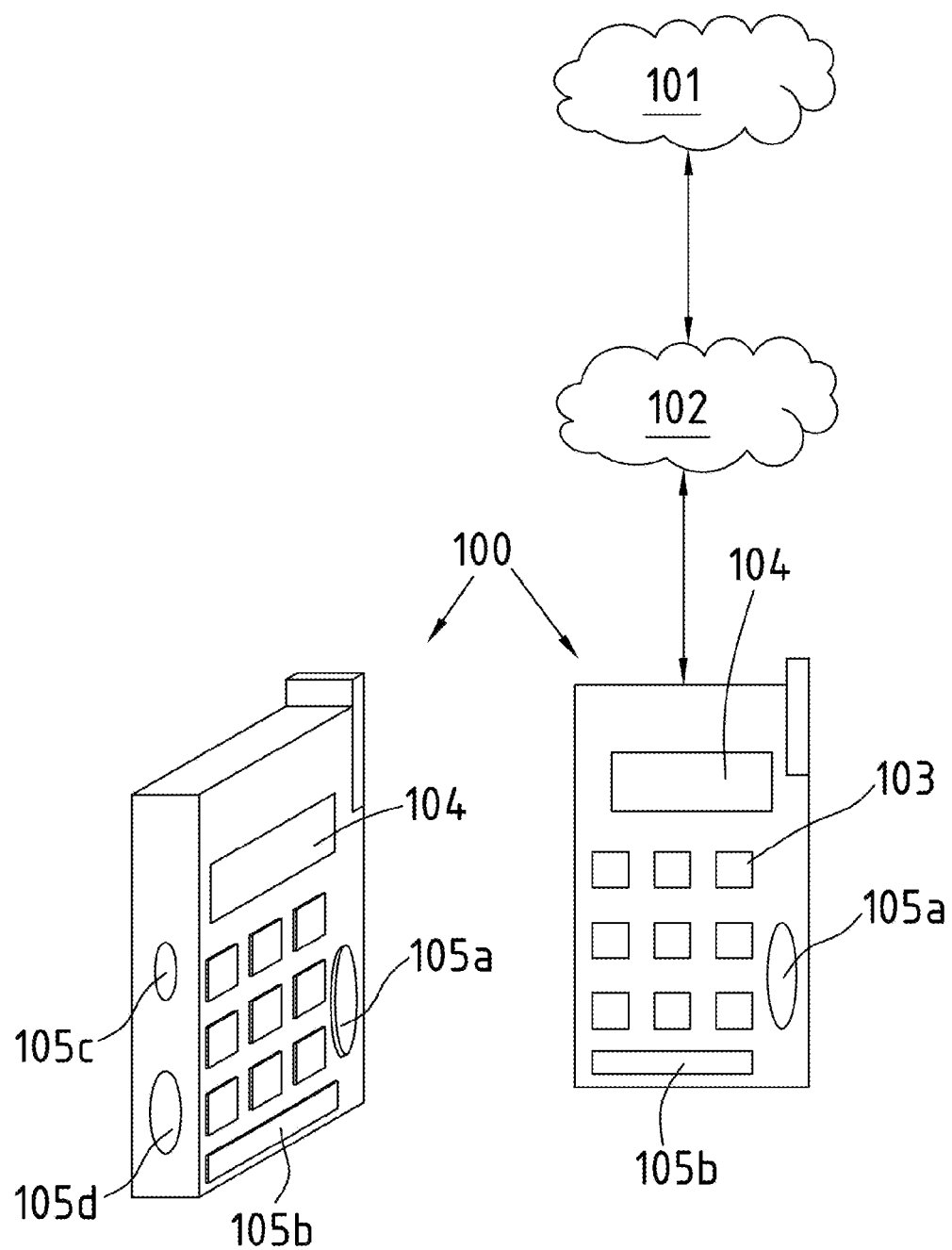
FIG. 1 is a block diagram of a mobile communication device according to an exemplary embodiment of the present invention.

FIG. 1 schematically depicts a mobile communication system comprising a mobile communication device 100, such as, for example, a cellular phone, a PDA (Personal Data Assistant) or the like, which is wirelessly connected to a PLMN (Public Land Mobile Network) 101 via a radio access network 102. The PLMN 101 is the core network of the mobile communication system operated by a mobile network operator and may be configured according to the GSM standard or according to the UMTS standard, for example. The radio access network 102 may be configured as a GERAN (GSM Edge Radio Access Network) according to the GSM standard or as an UTRAN (Universal Terrestrial Radio Access Network) according to the UMTS standard, for example.

As a conventional mobile telephone the mobile communication device 100 comprises a key pad 103 for entering numbers and letters as well as a display 104 to display messages and information for the user of the mobile communication device. In contrast to conventional mobile telephones the mobile communication device 100 is provided with a plurality of sensors 105a to 105d. The sensors 105a to 105d are located at positions on the outside of the mobile communication device 100. The user generally touches these positions when he utilizes the mobile communication device 100. In FIG. 1 the mobile communication device 100 is shown in a front view as well as in a perspective view from the side. From the front view it becomes apparent that the sensors 105a and 105b are located on the front face of the mobile communication device 100. The perspective view illustrates that the sensors 105c and 105d are located on one side face 106 of the mobile communication device 100. The reason is that a right-handed user touches the side face 106 with his fingers where the sensors 105c and 105d are located. The sensors 105 as such are known in the prior art and are capable to measure a set of biological and/or medical data of the user of the mobile communication device including blood pressure, heartbeat frequency, body temperature and some blood values. The captured biological and/or medical data can be displayed on the display 104 upon user request. In addition to that, the biological and/or medical data are stored in an internal memory of the mobile communication device enabling to build a kind of history of the captured data over an extended period of time.

Simple interpretations of the captured data can be made locally by a processor inside of the mobile communication device 100. Examples of such simple interpretations are the comparison of the actual heartbeat frequency and/or blood pressure when they exceed a pre-determined threshold value. In such a case the user may be notified by acoustic or optical messages reminding him to take appropriate measures to avoid health risks. Besides these kinds of simple interpretations it is also possible that the mobile communication device 100 transfers the captured data to a server via the mobile communication network 101 where the data are stored and interpreted by more sophisticated software applications running on the server. In this kind of situation the communication device acts as in the same time as a device for capturing the data and as a modem for a transmission of the data to the remote server.

Figure 2:
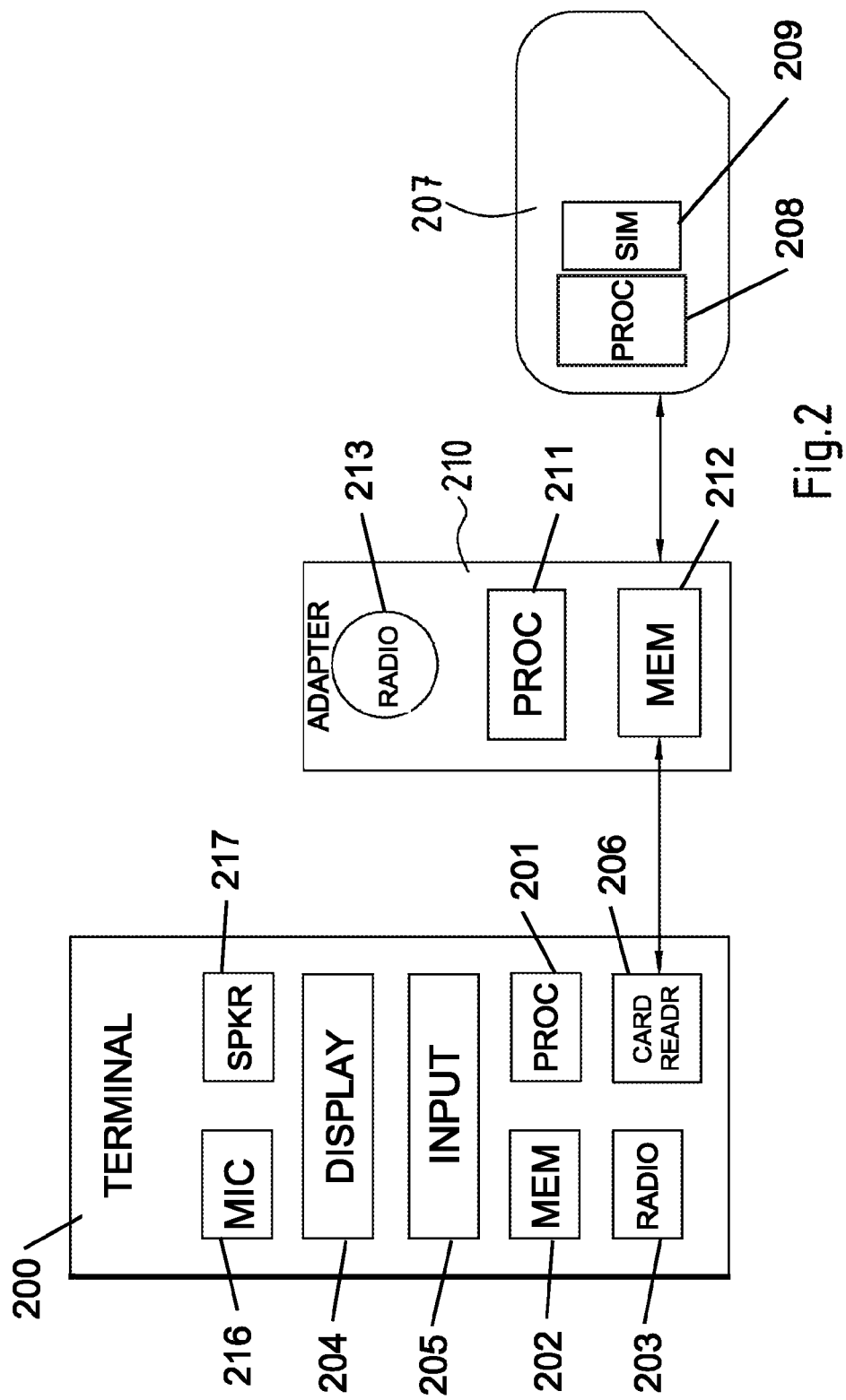
FIG. 2 is a block diagram of the functional blocks of the mobile communication device shown in FIG. 1.

FIG. 2 shows a schematic block diagram of the mobile communication device 100. The mobile communication device 100 comprises a mobile terminal 200 including a main processor 201 for controlling the operation of the mobile terminal 200. A memory unit 202 is coupled to the main processor 201 for storing data and applications that can be run on the main processor 201. Furthermore, the mobile terminal 200 comprises one or more communication interfaces. Particularly, the mobile terminal 200 provides a radio interface 203 for connecting the mobile terminal 200 wirelessly to a mobile communication network.

For capturing acoustic signals, particularly for capturing speech from the user of the mobile terminal 200, the mobile terminal 200 comprises a microphone 216. For outputting acoustic signals, the mobile terminal 200 comprises a loudspeaker 217. Moreover, the mobile terminal 200 comprises a display unit 204 and an input unit 205, which can be operated by the user of the mobile communication device 100. The input unit 205 may be configured as a keypad such as the keypad 103 shown in FIG. 1.

Using a card reader unit 206, the mobile terminal 200 can be connected to a subscriber identity module 207 to form the mobile communication device 100. The subscriber identity module 207 is a so-called smart card, which can be inserted into a card receptacle of the mobile terminal 200 that holds the card in a position, in which its contact elements are connected to corresponding contact elements of the card reader unit 206 of the mobile terminal 200. The card receptacle and the card reader unit 206 are usually arranged within a battery compartment of the mobile terminal 200, which is accessible by the mobile user.

The subscriber identity module 207 may be configured as a subscriber identity module (SIM) according to the GSM standard or as a universal subscriber identity module (USIM) according to the UMTS standard, for example. It comprises a microprocessor 208 and a non-volatile memory 209 and stores pre-configured user-related and network-related data, particularly data identifying the mobile user and data for authenticating the user or his mobile communication device 100 to the mobile network 101. Moreover, it may store personal data of the mobile user, such as for example, contact data, notes or messages received in the mobile communication device 100.

In the present embodiment, the subscriber identity module 207 is not connected directly to the mobile terminal 200 or its card reader unit 206, but via an adapter module 210. The adapter module 210 comprises a microprocessor 211 and a memory unit 212 for storing data and applications that can be run on the microprocessor 211. When connected between the mobile terminal 200 and the subscriber identity module 207, the adapter module 210 acts as a so-called man in the middle device. Hence, communication signals between the mobile terminal 200 and the subscriber identity module 207 are exchanged via the adapter module 210 that forwards data messages from the mobile terminal 200 to the subscriber identity module 207 and vice versa.

The adapter module 210 may be capable of manipulating or modifying the data exchange between the mobile terminal 200 and the subscriber identity module 207. Moreover, the adapter module 210 is capable of initiating a communication with the mobile terminal 200 and/or the subscriber identity module 207 to interact proactively with the mobile terminal 200 and with the subscriber identity module 207. For this purpose, the adapter module 210 may implement the SIM application toolkit (SAT) specified in the specification GSM 11.14 of the 3rd generation project partnership (3GPP), if the subscriber identity module 207 is a SIM according to the GSM standard or the adapter module 210 may implement the USIM application toolkit (USAT) specified in the specification TS 31.111 of the 3GPP, if the subscriber identity module 207 is a USIM. The SAT, or USAT allows the subscriber identity module 207 to access functions of the mobile terminal 200 and particularly comprises so-called proactive commands by which the subscriber identity module 207 is able to access the functions of the mobile terminal 200 on its own initiative. By implementing the SAT or USAT in the adapter module 210, the adapter module 210 is able to access the functions of the mobile terminal 200 in the same way as the subscriber identity module 207. Also other kinds of applications running on the processor 211 are programmable. These applications are not necessarily related to the subscriber identity module 207.

For connecting the adapter module 210 between the mobile terminal 200 and the subscriber identity module 207, the adapter module 210 comprises a contacting element, which can be inserted into the card receptacle of the mobile terminal 200 and which includes electric contacts for contacting the contact elements of the card reader unit 206. Further electrical contacts are provided for contacting the electric contacts of the subscriber identity module 207. The electric contacts for connecting the adapter module 210 to the mobile terminal 200 and the electric contacts for connecting the adapter module 210 are connected to the micropro-cessor 211 of the adapter module 210.

As one of the electric contacts of the card reader unit 206 of the mobile terminal 200 acts as a power supply for the subscriber identity module 207, the adapter module 210 can also be supplied with power via this electric contact. Moreover the adapter module 210 is able to forward data received via an electric contact of the card reader to the corresponding electric contact of the subscriber identity module 207 and vice versa. The forwarded data may be modified by the microprocessor 211 of the adapter module 210 or the adapter module 210 may leave the data unmodified, thereby allowing a normal communication between the mobile terminal 200 and the subscriber identity module 207. Moreover, the proactive commands are sent from adapter module 210 to the mobile terminal 100 via the electric contact, which is provided for sending commands from the subscriber identity module 207 to the mobile terminal 210.

In one exemplary embodiment, the adapter module 210 comprises a thin contacting element, which has essentially the same shape as the subscriber identity module 207 and which can be inserted into the card receptacle of the mobile terminal 200 between the electric contacts of the card reader unit 206 and the subscriber identity module 207. On one surface, the contacting element comprises contact elements for contacting the contact elements of the subscriber identity module 207 and on the opposite surface, contact elements are arranged for contacting the contact elements of the card reader unit 206. The contact elements are connected to the microprocessor 211 of the adapter module 210. The microprocessor 211 and the memory unit 212 of the adapter module 210 may be mounted on a circuit board, which is connected to the contacting element with a flexible wire, thereby allowing placing the circuit board into the battery compartment of the mobile terminal 200 together with the battery. As an alternative, the microprocessor 211 and the memory unit 212 may be included in a chip that is mounted on the contacting element. In this embodiment the subscriber identity module 207 is being provided with a cutting for accepting the chip.

In another embodiment, the adapter module 210 comprises a contacting element that has essentially the same shape and thickness as the subscriber identity module 207 and that can be inserted into the card receptacle of the mobile terminal 200 to contact the contact elements of the card reader unit 206. The contacting element is connected to a circuit board via one or more flexible wires. The microprocessor 211 and the memory unit 212 are mounted on the circuit board and in addition, the circuit board comprises a card reader unit connected to the microprocessor 211 for receiving the adapter module 210 to the subscriber identity module 207. The circuit board is thin enough to place it into the battery compartment of the mobile terminal 200.

The adapter module 210 also comprises a radio interface 213 for connecting the adapter module 210 to other devices provided with a corresponding radio interface. The radio interface 213 is controlled by the microprocessor 211 of the adapter module 210 and may contain a digital radio and all other necessary devices to generate radio signals according to the specification of a local wireless communication network between the mobile communication device 100 and the other devices.

Figure 3:
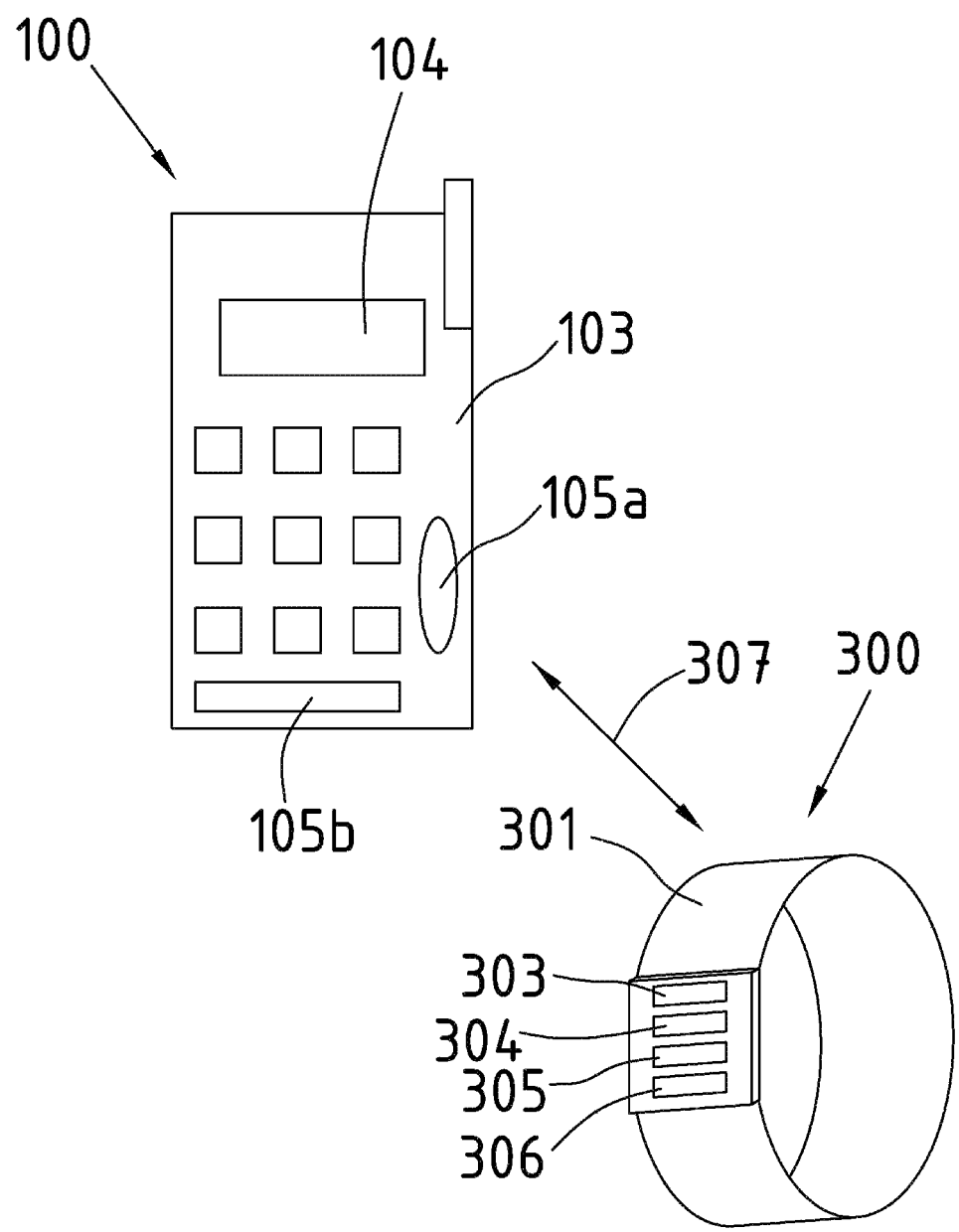
FIG. 3 is a block diagram of the mobile communication device of FIG. 1 and a sensor which is separated of the mobile communication device.

FIG. 3 shows the mobile communication device 100 which is communicating with its secondary radio interface 213 with a bracelet 300 which comprises a corresponding radio interface which is not shown in FIG. 3. The bracelet as a whole is labelled with the reference number 300 and comprises a wristband 301 as well as housing 302 accommodating one sensor or a plurality of sensors adapted to capture biological and/or medical data of the person wearing the bracelet 300. In addition to that the housing 302 also accommodates a radio interface 303 corresponding to the radio interface 213 of the adapter module 210. Typically the radio interface 213 of the adapter module 210 uses existing radio standards such as ZigBee or near field communication to communicate with the radio interface 303 of the bracelet 300. The housing 302 further comprises a processor 304 which manages the data exchange between the one sensor or several sensors 305 and the radio interface contained in the housing 302. Finally, the housing 302 accommodates a memory 306 to store the data captured by the sensor(s) 305. This feature is particularly useful if the data cannot be transferred for a certain time to the mobile communication device 100. The memory 306 acts as a buffer that can prevent a total loss of the data in such a situation. In another embodiment of the present invention the radio interface may operate according to the Bluetooth standard to exchange a data between the mobile communication device 100 and the bracelet 300. The two-way communication between the mobile communication device and the bracelet 300 is indicated in FIG. 3 by a double headed arrow 307 symbolizing the local wireless communication network between the mobile communication device 100 and the other devices.

The bracelet 300 is only one exemplary embodiment of sensors which are carried by the user of the mobile communication device. The present invention encompasses also other types of sensors which are carried on the body of the user to capture relevant biological and/or medical data. In most cases it is convenient to establish a wireless communication link between the adapter module 210 and the sensor(s) 305. However, in another embodiment of the invention a wired communication link between the adapter module 210 and the sensor(s) 305 is provided which is technically simpler than a wireless communication link.

An application running on the processor 211 of the adapter module 210 manages the data communication between the mobile communication device 100 and the bracelet 300. The application running on the processor 211 of the adapter module 210 is also arranged to store the captured data in the memory 212 of the adapter module 210 as well as optionally initiating a connection to a remote server via the wireless networks 102 and 101. In this way the data are transferred to the server where more sophisticated application requiring more memory and processing power can be utilized to perform the interpretation of the data captured by the sensors 305. It is to be noted that the described embodiment of the present invention has no impact on the hardware and the software of the mobile terminal 200 itself. Contrary to conventional mobile devices capturing biological and/or medical data of the user the device according to the invention does not require the integration of a new application into the hard- and software of the mobile terminal 200. Consequently it is also possible to upgrade pre-existing mobile terminals 200 to a mobile communication device which is capable to capture biological and/or medical data of the user of the mobile telephone.

Figure 4:
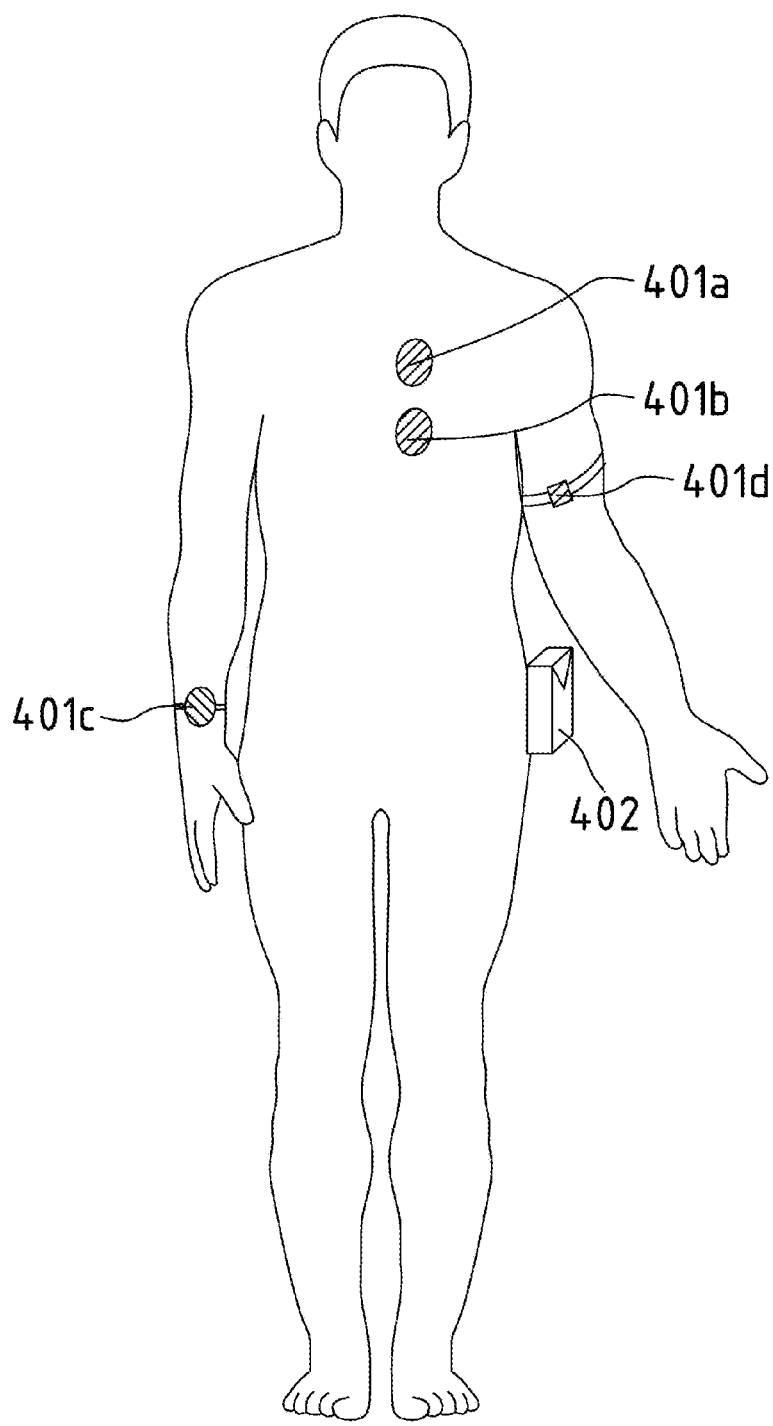
FIG. 4 is a diagram of a human body on which exemplary locations for sensors for capturing biological and/or medical data are identified.

FIG. 4 shows another embodiment of the present invention utilizing a plurality of sensors 401a to 401d to capture a large variety of biological and/or medical data of the user of the mobile communication device 100. The sensors 401a and 401b are glued or fixed with tape directly on to the body of the user while the sensors 401c and 401d are carried by wrist bands on the arms of the body. A person skilled in the measurement of biological and/or medical data can easily identify other locations on the body of the user where certain data can be captured in a convenient and reliable way. All sensors are similar to the structure that has been described in connection with FIG. 3 and the wrist band 300. Consequently all sensors 401a to 401d are capable to communicate independently with the mobile communication device 100 which is carried in a bag 402 by the user. In this embodiment the communication device 100 may or may not be equipped with additional sensors 105 to 105d which are located on the outside of the communication device 100. Every time the user takes the communication device 100 in his hands e.g. to make a telephone call he or she touches the sensors 105a to 105d and enables in this way the generation of additional biological and/or medical data.

What is claimed is:

1. A mobile communication device, comprising:
   a mobile terminal;
   an input unit at the mobile terminal;
   a display at the mobile terminal; and
   a processing unit at the mobile terminal being connected with a subscriber identity module and with an adapter module, the subscriber identity module being connected with the mobile terminal via the adapter module, wherein the adapter module comprises a microprocessor, and a memory unit for storing data, and applications that can be run on the microprocessor, is in communication with at least one sensor capturing biological and/or medical data of a user of the mobile communication device and the microprocessor being configured to run an application for reading out the at least one sensor, or a plurality of sensors, connected to the mobile communication device.

2. The mobile communication device recited in claim 1, wherein the at least one sensor comprises a plurality of sensors.

3. The mobile communication device recited in claim 1, wherein the at least one sensor is located on an outside of the mobile communication device to provide physical contact with the user who utilizes the communication device.

4. The mobile communication device recited in claim 1, wherein the at least one sensor is not located on the mobile communication device.

5. The mobile communication device recited in claim 4, wherein the at least one sensor is integrated in a device which is separate of the mobile communication device.

6. The mobile communication device recited in claim 5, wherein the at least one sensor is separate of the mobile communication device and is connected to the adapter module by a data communication link.

7. The mobile communication device recited in claim 6, wherein the communication link comprises a wired or wireless data communication link.

8. The mobile communication device recited in claim 7, wherein the wireless data communication link is a communication link according to the ZigBee or NFC standard.

9. The mobile communication device recited in claim 1, wherein the adapter module comprises a contacting element suitable to be inserted into a card receptacle of the mobile terminal, electrical contacts for contacting contact elements of a card reader unit of the mobile terminal, and electrical contacts for contacting the electrical contacts of the subscriber identity module.

10. A system, comprising:
   a mobile communication device that comprises a subscriber identity module;
   a sensor separate from the mobile communication device; and
   an adapter module comprising a microprocessor, and a memory unit for storing data and applications that can be run on the microprocessor, the adapter module being connected to the subscriber identity module, the microprocessor being configured to run an application for reading a sensor capturing biological and/or medical data of a user of the mobile communication device, wherein the sensor is connected to the adapter module by data communication link.

11. The system recited in claim 10, wherein the adapter module and sensor are each connected to a radio interface.

12. The system recited in claim 11, wherein the radio interface is an interface according to the ZigBee and/or NFC standard.

13. A mobile communication device comprising:
   a mobile terminal comprising an input unit, a display, a processing unit;
   a subscriber identity module; and
   an adapter module to connect the subscriber module with the mobile terminal, wherein the adapter module comprises a microprocessor, and a memory unit for storing data, and applications that can be run on the microprocessor, the adapter module being in communication with at least one sensor capturing biological and/or medical data of a user of the mobile communication device and the microprocessor is configured to run an application for reading out the at least one sensor, or a plurality of sensors, connected to the mobile communication device.

* * * * *